US007959683B2

(12) United States Patent
Semler et al.

(10) Patent No.: US 7,959,683 B2
(45) Date of Patent: Jun. 14, 2011

(54) PACKED DEMINERALIZED CANCELLOUS TISSUE FORMS FOR DISC NUCLEUS AUGMENTATION, RESTORATION, OR REPLACEMENT AND METHODS OF IMPLANTATION

(75) Inventors: Eric J. Semler, Piscataway, NJ (US); Judith I. Yannariello-Brown, Somerset, NJ (US); Morris L. Jacobs, Newtown, PA (US); Karen Roche, Stillwater, MN (US); Steve Wolfe, Woodbury, MN (US)

(73) Assignees: Musculoskeletal Transplant Foundation, Edison, NJ (US); Spineology, Inc., St. Paul, MN (US)

( * ) Notice: Subject to any disclaimer, the term of this patent is extended or adjusted under 35 U.S.C. 154(b) by 837 days.

(21) Appl. No.: 11/878,269

(22) Filed: Jul. 23, 2007

(65) Prior Publication Data
US 2008/0027546 A1 Jan. 31, 2008

Related U.S. Application Data

(60) Provisional application No. 60/832,956, filed on Jul. 25, 2006.

(51) Int. Cl.
*A61F 2/28* (2006.01)
(52) U.S. Cl. ............... 623/23.61; 623/17.11; 623/23.63
(58) Field of Classification Search ............ 606/60, 606/246–249; 623/17.11–17.16, 23.61, 23.63, 623/919
See application file for complete search history.

(56) References Cited

U.S. PATENT DOCUMENTS

| 3,867,728 A | 2/1975 | Stubstad et al. |
| 3,875,595 A | 4/1975 | Froning |
| 4,349,921 A | 9/1982 | Kuntz |
| 4,399,814 A | 8/1983 | Pratt et al. |
| 4,466,435 A | 8/1984 | Murray |
| 4,488,549 A | 12/1984 | Lee et al. |
| 4,501,269 A | 2/1985 | Bagby |
| 4,576,152 A | 3/1986 | Muller et al. |
| 4,625,722 A | 12/1986 | Murray |
| 4,655,749 A | 4/1987 | Fischione |
| 4,655,777 A | 4/1987 | Dunn et al. |
| 4,735,625 A | 4/1988 | Davidson |
| 4,751,921 A | 6/1988 | Park |
| 4,755,184 A | 7/1988 | Silverberg |
| 4,772,287 A | 9/1988 | Ray et al. |

(Continued)

FOREIGN PATENT DOCUMENTS
DE 29908794 U1 * 9/1999
(Continued)

OTHER PUBLICATIONS

Kuslich et al., "The Orgin of Low Back Pain and Sciatica: A Microsurgical Investigation," reprinted from *Microsurgery of the Lumbar Spine*, R. W. Williams et al. (Eds.) pp. 1-7 (1990).

(Continued)

*Primary Examiner* — Eduardo C Robert
*Assistant Examiner* — Christina Negrelli
(74) *Attorney, Agent, or Firm* — Greenberg Traurig, LLP

(57) ABSTRACT

A composition for spinal disc repair comprising a plurality of uniformly shaped demineralized cancellous bone pieces ranging in size from about 2.0 mm to about 4.0 mm loaded into a porous mesh container with the cancellous bone pieces being treated so that they are not osteoinductive and are packed in the porous mesh container under compression forces.

62 Claims, 3 Drawing Sheets

U.S. PATENT DOCUMENTS

| | | |
|---|---|---|
| 4,815,454 A | 3/1989 | Dozier, Jr. |
| 4,834,757 A | 5/1989 | Brantigan |
| 4,863,477 A | 9/1989 | Monson |
| 4,865,604 A | 9/1989 | Rogozinski |
| 4,904,260 A | 2/1990 | Ray et al. |
| 4,911,718 A | 3/1990 | Lee et al. |
| 4,932,969 A * | 6/1990 | Frey et al. |
| 4,932,975 A | 6/1990 | Main et al. |
| 4,936,848 A | 6/1990 | Bagby |
| 5,015,255 A | 5/1991 | Kuslich |
| 5,047,055 A | 9/1991 | Bao et al. |
| 5,053,049 A | 10/1991 | Campbell |
| 5,059,193 A | 10/1991 | Kuslich |
| 5,071,040 A | 12/1991 | Laptewicz, Jr. |
| 5,108,438 A | 4/1992 | Stone |
| 5,171,280 A | 12/1992 | Baumbgartner |
| 5,171,281 A | 12/1992 | Parsons et al. |
| 5,181,918 A | 1/1993 | Brandhorst et al. |
| 5,192,325 A | 3/1993 | Kijima et al. |
| 5,192,326 A | 3/1993 | Bao et al. |
| 5,192,327 A | 3/1993 | Brantigan |
| 5,282,863 A | 2/1994 | Burton |
| 5,298,254 A | 3/1994 | Prewett et al. |
| 5,303,718 A | 4/1994 | Krajicek |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,306,311 A | 4/1994 | Stone et al. |
| 5,314,476 A | 5/1994 | Prewett et al. |
| 5,314,477 A | 5/1994 | Marnay |
| 5,314,478 A | 5/1994 | Oka et al. |
| 5,324,273 A | 6/1994 | Discko, Jr. |
| 5,431,654 A | 7/1995 | Nic |
| 5,439,684 A | 8/1995 | Prewett et al. |
| 5,443,514 A | 8/1995 | Steffee |
| 5,501,687 A | 3/1996 | Willert et al. |
| 5,507,813 A | 4/1996 | Dowd et al. |
| 5,545,222 A | 8/1996 | Bonutti |
| 5,549,679 A | 8/1996 | Kuslich |
| 5,571,189 A | 11/1996 | Kuslich |
| 5,577,517 A | 11/1996 | Bonutti |
| 5,658,341 A | 8/1997 | Delfosse |
| 5,697,932 A | 12/1997 | Smith et al. |
| 5,702,454 A * | 12/1997 | Baumgartner |
| 5,711,957 A | 1/1998 | Patat et al. |
| 5,718,707 A | 2/1998 | Mikhail |
| 5,755,797 A * | 5/1998 | Baumgartner |
| 5,782,919 A | 7/1998 | Zdeblick et al. |
| 5,814,084 A | 9/1998 | Grivas et al. |
| 5,824,087 A | 10/1998 | Aspden et al. |
| 5,842,786 A | 12/1998 | Solomon |
| 5,863,297 A | 1/1999 | Walter et al. |
| 5,899,939 A | 5/1999 | Boyce et al. |
| 5,910,315 A | 6/1999 | Stevenson et al. |
| 5,972,368 A | 10/1999 | McKay |
| 5,989,289 A | 11/1999 | Coates et al. |
| 5,997,581 A | 12/1999 | Khalili |
| 5,997,582 A | 12/1999 | Weiss |
| 6,004,325 A | 12/1999 | Vargas, III |
| 6,019,765 A | 2/2000 | Thornhill et al. |
| 6,022,376 A | 2/2000 | Assell et al. |
| 6,025,538 A | 2/2000 | Yaccarino, III |
| 6,027,743 A | 2/2000 | Khouri et al. |
| 6,039,762 A | 3/2000 | McKay |
| 6,090,998 A | 7/2000 | Grooms et al. |
| 6,096,081 A | 8/2000 | Grivas et al. |
| 6,123,731 A | 9/2000 | Boyce |
| 6,132,465 A | 10/2000 | Ray et al. |
| 6,183,518 B1 | 2/2001 | Ross et al. |
| 6,200,347 B1 | 3/2001 | Anderson et al. |
| 6,224,630 B1 | 5/2001 | Bao et al. |
| 6,240,926 B1 | 6/2001 | Chin Gan et al. |
| 6,245,107 B1 | 6/2001 | Ferree |
| 6,261,586 B1 | 7/2001 | McKay |
| 6,270,528 B1 | 8/2001 | McKay |
| 6,294,187 B1 | 9/2001 | Boyce et al. |
| 6,379,385 B1 | 4/2002 | Kalas et al. |
| 6,383,221 B1 | 5/2002 | Scarborough et al. |
| 6,395,034 B1 | 5/2002 | Suddaby |
| 6,398,811 B1 | 6/2002 | McKay |
| 6,419,707 B1 | 7/2002 | Leclercq |
| 6,432,436 B1 | 8/2002 | Gertzman et al. |
| 6,437,018 B1 | 8/2002 | Gertzman et al. |
| 6,443,988 B2 | 9/2002 | Felt et al. |
| 6,447,514 B1 | 9/2002 | Stalcup et al. |
| 6,458,144 B1 | 10/2002 | Morris et al. |
| 6,458,158 B1 | 10/2002 | Anderson et al. |
| 6,554,803 B1 | 4/2003 | Ashman |
| 6,599,293 B2 | 7/2003 | Tague et al. |
| 6,620,162 B2 | 9/2003 | Kuslich et al. |
| 6,620,169 B1 | 9/2003 | Peterson et al. |
| 6,620,196 B1 | 9/2003 | Trieu |
| 6,626,912 B2 | 9/2003 | Speitling |
| 6,632,247 B2 | 10/2003 | Boyer, II et al. |
| 6,645,213 B2 | 11/2003 | Sand et al. |
| 6,652,593 B2 | 11/2003 | Boyer et al. |
| 6,676,664 B1 | 1/2004 | Al-Assir |
| 6,692,528 B2 | 2/2004 | Ward et al. |
| 6,696,073 B2 | 2/2004 | Boyce et al. |
| 6,712,853 B2 | 3/2004 | Kuslich |
| 6,758,863 B2 * | 7/2004 | Estes et al. |
| 6,761,739 B2 | 7/2004 | Shepard |
| 6,767,369 B2 | 7/2004 | Boyer et al. |
| 6,783,546 B2 | 8/2004 | Zucherman et al. |
| 6,855,167 B2 | 2/2005 | Shimp et al. |
| 6,902,578 B1 | 6/2005 | Anderson et al. |
| 6,991,653 B2 | 1/2006 | White et al. |
| 7,025,771 B2 | 4/2006 | Kuslich et al. |
| 7,044,968 B1 | 5/2006 | Yaccarino, III et al. |
| 7,048,762 B1 | 5/2006 | Sander et al. |
| 7,048,765 B1 | 5/2006 | Grooms et al. |
| 7,056,345 B2 | 6/2006 | Kuslich |
| 7,087,082 B2 | 8/2006 | Paul et al. |
| 7,094,258 B2 | 8/2006 | Lambrecht et al. |
| 7,115,146 B2 | 10/2006 | Boyer et al. |
| 7,179,299 B2 | 2/2007 | Edwards et al. |
| 7,220,282 B2 | 5/2007 | Kuslich |
| 7,226,481 B2 | 6/2007 | Kuslich |
| 7,226,482 B2 | 6/2007 | Messerli et al. |
| 7,309,359 B2 | 12/2007 | Trieu et al. |
| 7,323,011 B2 | 1/2008 | Shepard et al. |
| 7,479,160 B2 | 1/2009 | Branch et al. |
| 7,537,617 B2 | 5/2009 | Bindsell et al. |
| 7,563,455 B2 | 7/2009 | McKay |
| 7,601,173 B2 | 10/2009 | Messerli et al. |
| 7,608,113 B2 | 10/2009 | Boyer et al. |
| 2001/0020188 A1 | 9/2001 | Sander |
| 2001/0031254 A1 | 10/2001 | Bianchi et al. |
| 2001/0039457 A1 | 11/2001 | Boyer, II et al. |
| 2001/0041941 A1 | 11/2001 | Boyer, II et al. |
| 2001/0043940 A1 | 11/2001 | Boyce et al. |
| 2001/0339458 | 11/2001 | Boyer, II et al. |
| 2002/0013600 A1 | 1/2002 | Scribner et al. |
| 2002/0016592 A1 | 2/2002 | Branch et al. |
| 2002/0026195 A1 | 2/2002 | Layne et al. |
| 2002/0035401 A1 | 3/2002 | Boyce et al. |
| 2002/0045942 A1 | 4/2002 | Ham |
| 2002/0068974 A1 | 6/2002 | Kuslich et al. |
| 2002/0077701 A1 | 6/2002 | Kuslich |
| 2002/0106393 A1 | 8/2002 | Bianchi et al. |
| 2002/0138143 A1 | 9/2002 | Grooms et al. |
| 2002/0147496 A1 | 10/2002 | Belef et al. |
| 2002/0156531 A1 | 10/2002 | Felt et al. |
| 2003/0023311 A1 * | 1/2003 | Trieu ........................ 623/17.16 |
| 2003/0093154 A1 | 5/2003 | Estes et al. |
| 2003/0144743 A1 | 7/2003 | Edwards et al. |
| 2004/0006348 A1 | 1/2004 | Peterson et al. |
| 2004/0054414 A1 | 3/2004 | Trieu et al. |
| 2004/0073314 A1 | 4/2004 | White et al. |
| 2004/0102850 A1 | 5/2004 | Shepard |
| 2004/0115172 A1 | 6/2004 | Bianchi et al. |
| 2004/0138748 A1 | 7/2004 | Boyer, II et al. |
| 2004/0143344 A1 | 7/2004 | Malaviya et al. |
| 2004/0215201 A1 | 10/2004 | Lieberman |
| 2004/0215343 A1 | 10/2004 | Hochschuler et al. |
| 2004/0225296 A1 * | 11/2004 | Reiss et al. ..................... 606/90 |

| | | | |
|---|---|---|---|
| 2004/0243242 | A1 | 12/2004 | Sybert et al. |
| 2005/0004672 | A1 | 1/2005 | Pafford et al. |
| 2005/0043808 | A1 | 2/2005 | Felt et al. |
| 2005/0055094 | A1 | 3/2005 | Kuslich |
| 2005/0065609 | A1 | 3/2005 | Wardlaw |
| 2005/0119754 | A1 | 6/2005 | Trieu et al. |
| 2005/0125077 | A1 | 6/2005 | Harmon et al. |
| 2005/0131417 | A1 | 6/2005 | Ahern et al. |
| 2005/0197707 | A1 | 9/2005 | Trieu et al. |
| 2005/0209602 | A1 | 9/2005 | Bowman et al. |
| 2005/0228498 | A1 | 10/2005 | Andres |
| 2005/0261681 | A9 | 11/2005 | Branch et al. |
| 2005/0261767 | A1 | 11/2005 | Anderson et al. |
| 2006/0030948 | A1 | 2/2006 | Manrique et al. |
| 2006/0149379 | A1 | 7/2006 | Kuslich et al. |
| 2006/0195193 | A1 | 8/2006 | Bloemer et al. |
| 2006/0235534 | A1 | 10/2006 | Gertzman et al. |
| 2006/0276907 | A1 | 12/2006 | Boyer et al. |
| 2007/0016214 | A1 | 1/2007 | Kuslich et al. |
| 2007/0067040 | A1 | 3/2007 | Ferree |
| 2007/0093912 | A1 | 4/2007 | Borden |
| 2007/0100450 | A1 | 5/2007 | Hodorek |
| 2007/0134291 | A1 | 6/2007 | Ting et al. |
| 2007/0168030 | A1 | 7/2007 | Edwards et al. |
| 2007/0260324 | A1* | 11/2007 | Joshi et al. .................. 623/23.51 |
| 2008/0015709 | A1 | 1/2008 | Evans et al. |
| 2008/0027546 | A1 | 1/2008 | Semler et al. |
| 2008/0045952 | A1 | 2/2008 | Kuslich |
| 2008/0113008 | A1 | 5/2008 | Roche |
| 2008/0305145 | A1 | 12/2008 | Shelby et al. |
| 2009/0099661 | A1 | 4/2009 | Bhattacharya et al. |
| 2009/0131986 | A1 | 5/2009 | Lee et al. |
| 2009/0297580 | A1 | 12/2009 | Dony et al. |

FOREIGN PATENT DOCUMENTS

| | | | |
|---|---|---|---|
| EP | 0277282 B1 * | 8/1991 | |
| EP | 0322334 B1 * | 2/1992 | |
| EP | 0517030 A2 | 12/1992 | |
| EP | 0621020 A1 * | 10/1994 | |
| EP | 0517030 B1 | 9/1996 | |
| EP | 1868539 A2 | 12/2007 | |
| EP | 2076220 A2 | 7/2009 | |
| FR | 2639823 A1 * | 8/1990 | |
| FR | 2662073 A1 * | 11/1991 | |
| GB | 2262238 A * | 6/1993 | |
| WO | WO 93/16664 A1 * | 9/1993 | |
| WO | WO 94/20047 A1 | 9/1994 | |
| WO | WO 99/08616 A1 * | 2/1999 | |
| WO | 99/09914 A1 | 3/1999 | |
| WO | WO 00/28907 A1 * | 5/2000 | |
| WO | 00/40177 A1 | 7/2000 | |
| WO | 02/064180 A1 | 8/2002 | |
| WO | WO 2006/113586 A2 | 10/2006 | |
| WO | WO 2006/113586 A3 | 9/2007 | |
| WO | WO 2008/013763 A2 | 1/2008 | |
| WO | WO 2008/013763 A3 | 6/2008 | |

OTHER PUBLICATIONS

Kuslich, "Microsurgical Nerve Root Decompression Utilizing Progressive Local Anethesia," reprinted from *Microsurgery of the Lumbar Spine*, R.W. Williams et al. (Eds.) pp. 139-147 (1990).

Kadoya, MD, et al., "Biomechangical and Morphologic Evaluation of a Three-Dimensional Fabric Sheep Artificial Intervertebrala Disc; In Vitro and In Vivo Analysis," SPINE vol. 26, No. 14, 1562-1569 (2001).

Non-Final Office Action mailed Dec. 8, 2009 in connection with U.S. Appl. No. 11/404,806.

Meakin et al., "Effect of removing the nucleus pulposus on the deformation of the annulus fibrosus during compression of the intervertebral disc", Journal of Biomechanics, vol. 33, (2000), pp. 575-580.

Non-final Office Action mailed on Oct. 10, 2007 in connection with U.S. Appl. No. 11/404,806.

Final Office Action mailed on Mar. 21, 2009 in connection with U.S. Appl. No. 11/404,806.

International Search Report mailed on Jul. 24, 2007 in connection with International Patent Application No. PCT/US2006/014342.

Written Opinion mailed on Jul. 24, 2007 in connection with International Patent Application No. PCT/US2006/014342.

International Preliminary Report on Patentability mailed on Oct. 16, 2007 in connection with International Patent Application No. PCT/US2006/014342.

International Search Report mailed on Apr. 29, 2008 in connection with International Patent Application No. PCT/US2007/016528.

Written Opinion mailed on Apr. 29, 2008 in connection with International Patent Application No. PCT/US2007/016528.

International Preliminary Report on Patentability mailed on Jan. 27, 2009 in connection with International Patent Application No. PCT/US2007/016528.

Canadian Office Action mailed on Jul. 20, 2009 in connection with Canadian Patent Application No. 2,604,622.

Australian Office Action mailed Feb. 6, 2009 in connection with Australian Patent Application No. 2006236548.

Written Opinion of the International Searching Authority dated Apr. 29, 2008 for International Application No. PCT/US07/16528 in the name of Musculoskeletal Transplant Foundation.

International Search Report from PCT/US2007/016528, International Publication Date Jan. 31, 2008.

International Search Report mailed on Jul. 24, 2007 in connection with International Patent Application No. PCT/US2006/014342.

Written Opinion mailed on Jul. 24, 2007 in connection with International Patent Application No. PCT/US2006/014342.

International Preliminary Report on Patentability mailed on Oct. 16, 2007 in connection with International Patent Application No. PCT/US2006/014342.

International Search Report mailed on Apr. 29, 2008 in connection with international Patent Application No. PCT/US2007/016528.

Written Opinion mailed on Apr. 29, 2008 in connection with International Patent Application No. PCT/US2007/016528.

International Preliminary Report on Patentability mailed on Jan. 27, 2009 in connection with International Patent Application No. PCT/US2007/016528.

Canadian Office Action mailed on Jul. 20, 2009 in connection with Canadian Patent Application No. 2,604,622.

Australian Office Action mailed Feb. 6, 2009 in connection with Australian Patent Application No. 2006236548.

Final Office action mailed on Jun. 23, 2010 in connection with U.S. Appl. No. 11/404,806.

Office Action mailed on May 31, 2010 in connection with Canadian Patent Application No. 2,604,622.

* cited by examiner

PACKED DEMINERALIZED CANCELLOUS TISSUE FORMS FOR DISC NUCLEUS AUGMENTATION, RESTORATION, OR REPLACEMENT AND METHODS OF IMPLANTATION

RELATED APPLICATIONS

This application claims priority from Provisional Application No. 60/832,956 filed Jul. 25, 2006.

FIELD OF THE INVENTION

The present invention generally relates to tissue forms used for augmentation, restoration or replacement of intervertebral discs.

A healthy intervertebral disc facilitates motion between pairs of vertebrae while absorbing and distributing compression forces and torque forces. The disc is composed of two parts; namely a tough outer ring (the annulus fibrosis) which holds and stabilizes a soft central core material (the nucleus pulposus) that bears the majority of the load forces.

The tissue form of the present invention is dense cancellous tissue, which may be derived from proximal and distal femur, proximal and distal tibia, talus, calcaneus, proximal humerus, patella, or ilium that is first fully demineralized, cleaned, treated such that the bone is non-osteoinductive, and then processed into small uniform geometries that may be either cuboidal, disc-shaped ("mini-discs"), or spherical. The relative sizes of these shapes are on the order of 1.0 mm to 4.0 mm in either length or diameter. The tissue forms, following demineralization, are compressible such that individual units can be packed tightly together in a confined space and when packed together behave mechanically as one coherent unit while providing suitable load-bearing properties in the disc nucleus. When confined in the disc space under normal loading conditions, this plurality of shaped units functions as an elastic body, which is deformable, yet resilient under dynamic loading and has intrinsic shape-memory properties.

BACKGROUND OF THE INVENTION

Minimally invasive surgery that is aimed to treat degenerative disc disease and preserve motion in the spine is currently under investigation. Since the onset of the degenerative cascade in the disc is typically associated with dehydration and volume loss in the nucleus pulposus, a potential early intervention step may involve adding mechanically suitable material to the nucleus pulposus at the first observable signs of discomfort and loss of disc height. This procedure would restore nuclear volume and pressure against the inner wall of the annulus fibrosus. In certain embodiments, a degree of decompression or "lift" between the adjacent vertebrae may be possible with this technique. In effect, the result would be the "re-inflation" of the annulus fibrosus, the annular "tire". Desirable outcomes of the procedure would be motion preservation, pain relief, and maintenance or restoration of disc height. Long-term re-modeling of the biological allograft-based implant into fibrous tissue or disc-like tissue would also provide favorable clinical outcomes.

At present, there are no nucleus pulposus replacement devices or augmentation technologies available for clinical usage in the United States. The Prosthetic Disc Nucleus (PDN), which is manufactured by Raymedica, was the first implant designed for nucleus replacement with the intention of attempting to restore natural mechanics in the spine. This implant is an acrylic-based hydrogel encased in a polyethylene jacket. While this technology has been implanted in over 3000 patients in Europe, significant issues regarding implant migration and implant hardening have been encountered. Other drawbacks in the design of this implant include the requirement of a substantial annulotomy and total nucleotomy as well as the inability of the implant to fill the entire nuclear cavity. In addition, the limited ability of the implant to swell inside the disc nucleus leads to high extrusion rates and inadequate load transfer of compressive forces in the disc nucleus to tensile forces on the annulus fibrosus.

Generally speaking artificial disc replacements falls into two general categories, total disc replacement and nuclear replacement. Total disc replacement devices have a number of problems; namely that they are large and non-compressible, require the removal of a large portion of the annulus and require a highly invasive surgical approach in order to be implanted. If these disc replacement devices do not remain firmly attached to the vertebral bodies, these implants can extrude or migrate from their intended position, cause significant complications and are very difficult to revise. The second category of disc replacement is nuclear replacement which is a form of partial disc replacement. Various types of methods and devices have been used to attempt to accomplish successful disc replacement.

U.S. Pat. No. 6,652,593 issued Nov. 25, 2003 is directed toward an osteoinductive implant comprising demineralized cancellous bone, which comprises a non-particulate bone. A unitary bone block is compressed into a smaller configuration such as a pellet and then hardened via drying. Upon re-hydration, the pellet will expand and assume its original shape inside a cavity. The implant is capable of being compressed and hardened into a first shape and then capable of expanding into a second shape larger than the first shape when re-softened and permitted to expand. The '593 implant is designed to be supplied either in geometries that fill correspondingly sized voids or in compressed initial geometries that are used to expand and fill any given shape smaller than or equal to their expanded size.

United States Patent Publication 2006/0030948 filed Sep. 21, 2005 is directed toward an osteogenic implant having a predetermined shaped formed of an aggregate of different sized elongate (possessing a high median length to median thickness ratio) bone particles.

United States Patent Publication No. 2004/0054414 filed on Sep. 18, 2002 is directed toward a method of augmenting an intervertebral disc nucleus by the surgical addition of a particulate collagen-based material. The collagen-based material, having a mean particle size ranging from 0.05 mm to 5 mm, may be injected in either a wet or dry state and may be supplemented with growth factors, proteoglycans, and cells. The '414 publication notes the use of demineralized bone matrix particles with sizes ranging from between 0.05 mm and 3 mm and the use of elongated cylindrical plugs. The plugs are described to be dehydrated and compressed in the radial direction and are inserted into delivery cannula for delivery into the disc space. The cylindrical plugs are delivered via extrusion through a cannula, and expand upon exiting the cannula by re-hydrating in the disc space. Examples 6 and 7 refer to the design and implementation of cylindrical plugs, which can be fabricated from solid, porous, or fibrous collagen.

Additional continuing United States Published Patent Applications Nos. 2005/0197707 filed Apr. 25, 2005 and 2005/0119754 filed Jan. 6, 2005 are based on the '414 publication. The '707 publication is directed toward the use of small particles of particulate fascia lata, particulate disc annulus material, annulus fibrosis, demineralized bone matrix and collagen which are added to the nucleus of an intervertebral disc. The '754 publication covers a method of augmenting an intervertebral disc nucleus by adding a plurality of collagen-rich tissue particles having a mean particle size between 0.25 and 1.0 mm to the disc plus a biologically active substance that promotes healing, repair or regeneration of the disc. This biologically active substance is further defined to be stem cells, hyaluronic acid, or growth factors while the collagen material is stated to be potentially allograft tissue. Radio contrast material may be added to enhance imaging of the injected material.

Another United States Patent Publication No. 2005/0055094 filed Nov. 5, 2003 discloses a system for replacing a disc nucleus involving an injection tube, a volume of fibrous tissue material to fill a nuclear cavity, and an insertion device for dispensing the tissue promoting material into the disc. Suitable fibrous tissue promoting material is listed as fascia, natural and/or man made polymeric fiber, fibrous tissue inducers such as talc, pharmaceuticals and/or minerals and fibrous tissue morphogenic protein.

U.S. Pat. No. 5,571,189 issued Nov. 5, 1996 describes an expandable bag filled with biological tissue for spinal fusion but does not show motion preservation in the spine.

The present inventive disc nucleus implant is a combination of multiple units of demineralized cancellous tissue treated to be non-osteoinductive that are designed to be small uniform geometric shapes which have the ability to pack together and act mechanically as a single unit under the compression of packing and not to comprise a non-particulate portion of a bone. The inventive tissue forms are compressed upon delivery into a cavity, but only to fit into the delivery device and not into a defined shape. In addition, the inventive tissue forms do not regain their original dimensions following the completion of the implantation procedure. In fact, the appropriate mechanical properties are only achieved if the mass of units is under compression and behaving as a coherent load-bearing material. The plurality of units that constitute the inventive implant, when taken together in an uncompressed state, have a geometry that is substantially larger than the cavity into which they are placed. Thus, the inventive implant takes on a smaller size in the confined space into which it is placed. Finally, the inventive allograft tissue form is treated to be non-osteoinductive, which achieves the desired outcome of motion preservation in the spine versus spinal fusion.

The noted prior art publications cite examples of various allograft tissues for usage such as demineralized bone matrix, disc annulus, fascia, ligaments, tendons, skin, or other connective tissues. The inventive tissue implant would not be provided in a dehydrated state and will be compressed axially inside the delivery tube rather than radially.

Advantages of the present inventive approach in comparison to other techniques include its ability to be entirely performed in a minimally invasive manner, total nucleotomy is not required and the implant size is adjustable by the volume of material that is added into the pouch. If desired an expandable pouch that is intended to hold the shaped units can be inserted into the disc nucleus through a small diameter hole and it will be enlarged with implant material to a size considerably larger than the insertion hole allowing the implant dimensions to conform to the existing cavity of the disc nucleus, with the porous pouch preventing the escape of material from the nuclear space while allowing the free transfer of fluid across its surface along with potential tissue ingrowth.

SUMMARY OF THE INVENTION

The implantable allograft tissue form represents uniform demineralized cancellous tissue units treated to be non-osteoinductive placed under compression which will allow them to pack closely in the confined space inside an annulus. Following implantation, when the units are tightly pressed together, the collective volume of implanted material can play a similar biomechanical role inside the disc as native nucleus pulposus. The implant represents a motion preserving alternative in the treatment of degenerative disc disease.

The steps of the surgical technique described herein represent a minimally invasive method for replacing or augmenting a spinal disc nucleus and includes the complete or partial removal of nucleus material, sizing of the resulting cavity, inserting an expandable, porous pouch into the nucleus through either an existing annular tear or through an annulotomy, filling the pouch with compressed small fully demineralized, non-osteoinductive cancellous bone tissue forms, and closing the pouch.

Another object of the invention is the usage of a biologic nuclear implant material which can experience tissue ingrowth and reorganization once implanted within the disc space. Alternatively, the biological and structural nature of the demineralized cancellous bone allows it to be a potential scaffold that can be potentially supplemented with cells and/or growth factors, which may induce matrix remodeling and the subsequent regeneration of nucleus-like tissue inside the disc following implantation.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention.

DETAILED DESCRIPTION OF THE INVENTION

Figures 1, 2:
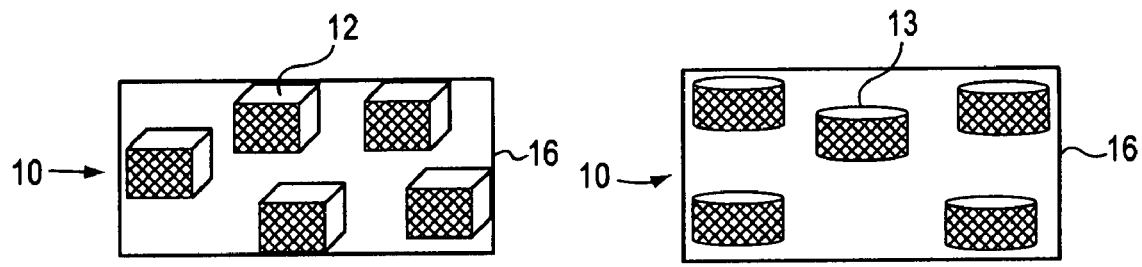
FIG. 1 shows an enlarged perspective view of a plurality of cancellous cube shaped units of the present invention in a schematic container.
FIG. 2 shows an enlarged perspective view of a plurality of cancellous disc shaped units of the present invention in a schematic container.

The preferred embodiment and best mode of the invention is seen in FIGS. 1 to 4. The present invention is directed toward an implant that is formed of a plurality of small, substantially demineralized cancellous bone shapes 10 that can be loaded and packed into a cannula or hollow rod and then inserted by packing the small shaped bone units into a disc nucleus in a non-dehydrated state. This packed material is to be utilized to augment, restore, or replace a disc nucleus. In a preferred embodiment, the tissue forms described within are to be delivered into an expandable porous mesh pouch 16 that has been pre-placed in the disc nucleus 20 through a small lateral opening 22 in the disc annulus such that the allograft material will be contained and not extrude out of the nucleus through an annular defect. The deformable nature of wet, demineralized cancellous bone will allow the tissue forms to pack tightly together in a confined space during delivery under sufficient pressure. A suitable amount of tissue is inserted so that the nuclear cavity is tightly filled and the resulting conglomerate implant acts as a single coherent mass under mechanical loading. This invention is implemented for patients with degenerative disc disease, particularly those in earlier stages of degeneration who still possess a competent annulus fibrosus.

Cancellous bone may be derived from proximal or distal femur, proximal or distal tibia, proximal humerus, talus, calceneus, patella, or ilium. Cancellous tissue is first processed into sheets or blocks, which preferably range in thickness of about 2 mm to 3 mm, although sheets of about 1.0 mm to about 4.0 mm can be used. Blood and lipids are flushed from the tissue using high pressure water. The cancellous tissue is then substantially demineralized in dilute acid until the bone contains less than 0.1% wt/wt residual calcium. Demineralization of the cancellous bone creates a material that is spongy and pliable in nature, yet still possesses elastic properties and shape memory following deformation.

Following decalcification, the cancellous tissue is cleaned and treated via chemical or thermal treatment or by high energy irradiation so that the cancellous tissue is non-osteoinductive.

In a preferred embodiment, the cancellous tissue is treated with hydrogen peroxide for at least 1 hour in order to further clean the tissue and to achieve a non-osteoinductive material. The tissue is then soaked in ethanol as an additional cleaning step. After these steps, the tissue is soaked in phosphate buffered saline (PBS) in order to restore the pH of the tissue within the range of 6.6 to 7.4. After these treatment steps, small units of cancellous tissue are fabricated from the cancellous sheets or blocks. The cancellous tissue form units have a defined shape that may be cuboidal, spherical, or discoid in nature and are loaded into filler tubes prior to implantation. The cancellous shapes may have a single dimension ranging from 1.0 mm to 4 mm and preferably are between 2 mm to 3 mm.

In the most preferred embodiment, the fully demineralized cancellous sheets are then cut into cube shaped tissue forms 12 with a side dimension of 2 mm to 3 mm using a chip press cutting device. The cancellous cubes are then lyophilized to less than 6% residual moisture. Following the dehydration step, a specific amount of dry cancellous cubes is weighted out ranging between 0.4 to 1.2 g. This amount of dry cancellous tissue is hydrated in excess water or saline and then loaded into a small diameter tube (2 mm to 4 mm in inner diameter) that is to be used to fill the disc nucleus during the surgical procedure.

In FIG. 2, disc shaped tissue forms 13 are formed using a mechanical press that acts as a multiple hole-punch. A preferred disc size is 2-3 mm in diameter and 2-3 mm in height. In another unit form spheres 14 are formed using a cutting device. A preferred sphere size is about 2-3 mm in diameter.

Figure 3:
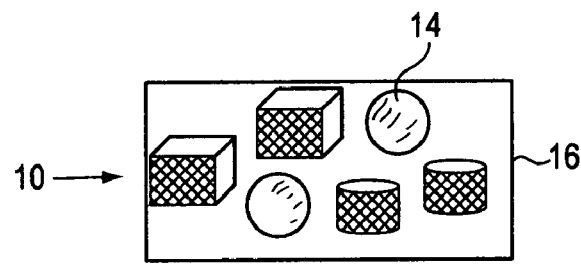
FIG. 3 shows an enlarged perspective view of a plurality of cancellous cubes, discs and sphere shaped units of the present invention in a schematic container.
Figure 4:
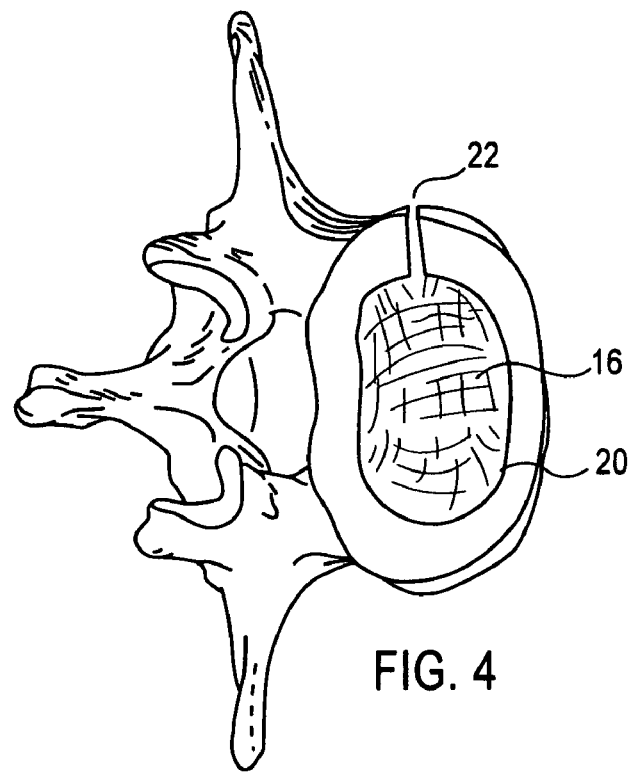
FIG. 4 shows a perspective view of a filled porous mesh pouch with demineralized cancellous tissue units placed in the disc nucleus following the creation of a lateral portal through the disc annulus.

FIG. 3 shows multiple unit configurations of cuboidal, spherical or discoid in shape used together. All of the shaped units are lyophilized to less than 6% residual moisture weighed in a dehydrated state, and then hydrated in excess water or saline before loading into an insertion tube or container.

A sufficient amount of cancellous bone is added to the expandable mesh pouch container 16 such that the volume of the nucleus is restored when the implant is packed so that it conforms to the shape of the nuclear cavity. Due to the design of the implant, the amount of filling material loaded into the bag may thus be customized for the specific size of the target nuclear cavity of the patient. In certain embodiments, the pouch may be filled with cancellous bone until it expands to a volume greater than that of the existing nuclear cavity, thereby providing a degree of decompression or "lift" between the two adjacent vertebrae. After the pouch is tightly packed with the shaped demineralized cancellous bone shaped units, the implant is designed to possess mechanical properties that withstand the compressive loads in the spine and facilitate load transfer from the nucleus to the annulus. Once filling is complete, pouches will be closed or sealed to prevent the escape of any cancellous tissue.

Figure 5:
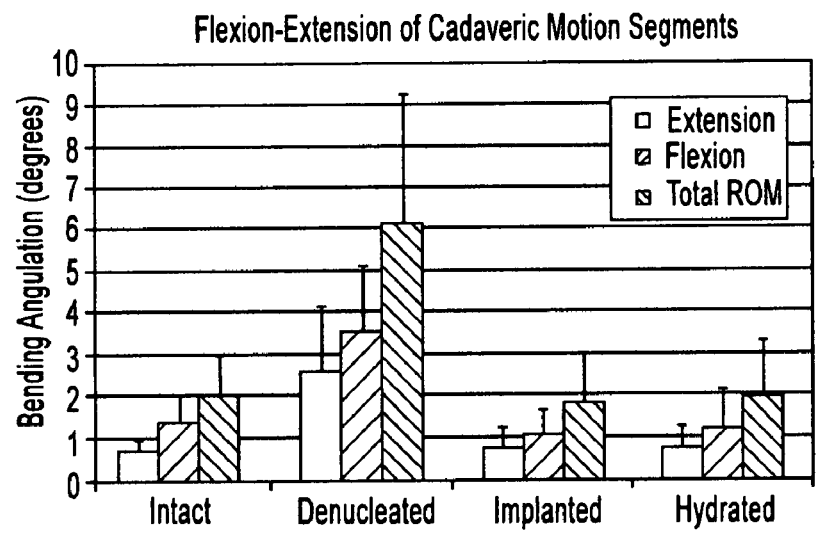
FIG. 5 is a chart showing the angular motion in flexion and extension of human cadaveric motion segments (a) for an intact disc, (b) the disc following nucleotomy, (c) the disc directly following implantation of the present invention and (d) the implanted disc after allowing 30 minutes for additional hydration.
Figure 6:
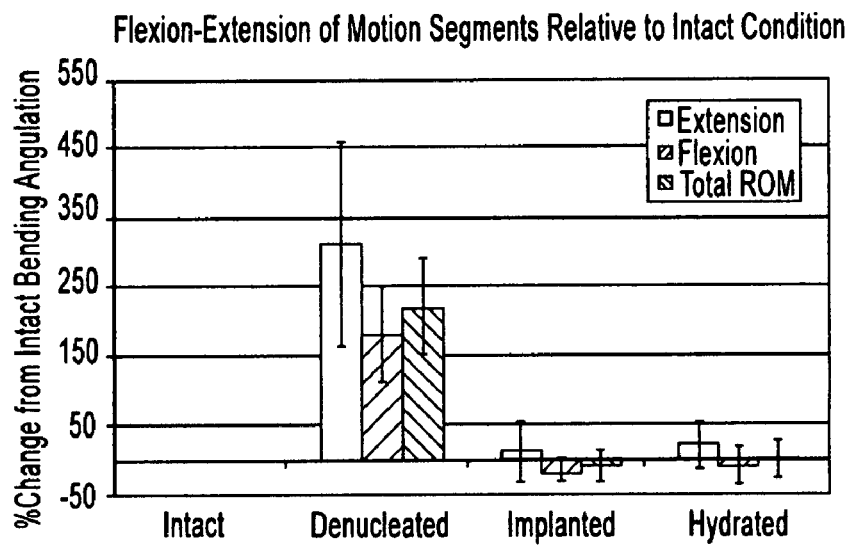
FIG. 6 is a chart showing the deviation of the motion segment flexibility in flexion-extension from the intact disc.
Figure 7:
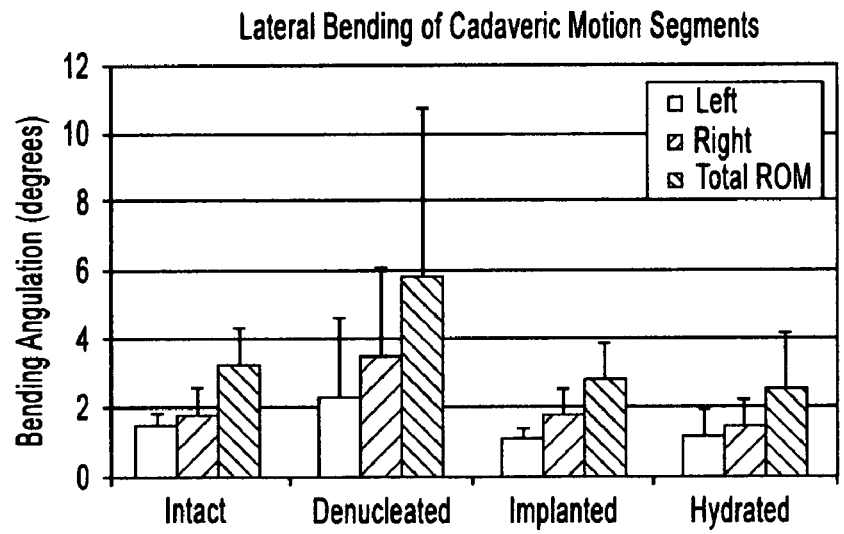
FIG. 7 is a chart showing the angular motion in left and right lateral bending of human cadaveric motion segments (a) for the intact disc, (b) the disc following nucleotomy, (c) the disc directly following implantation of the present invention, and (d) the implanted disc after allowing 30 minutes for additional hydration.
Figure 8:
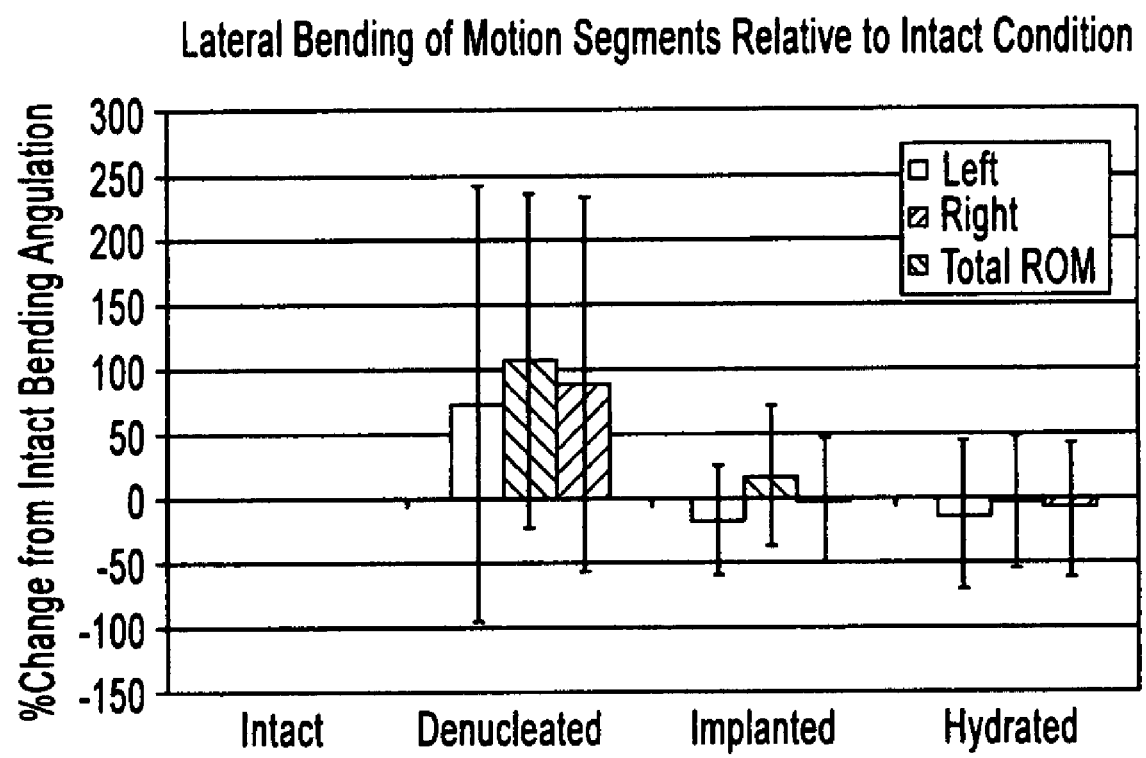
FIG. 8 is a chart showing the deviation of the motion segment flexibility in lateral bending from the intact disc.

As shown in FIGS. 5 and 6, disc-shaped fully demineralized allograft cancellous bone units (sized 3 mm diameter×3 mm height) were loaded into an expandable polyester mesh in situ at a packing density ranging from between 1.50 to 1.60 g/cc based on the hydrated mass of the tissue and the measured cavity size of the denucleated disc. The figures represent the acute restoration of stability to the spinal motion segment following nucleotomy and the implantation of the inventive implant device. Testing was performed on each cadaveric motion segment (either L2-L3 or L4-L5) at four different stages: the intact disc, the disc following nucleotomy, the denucleated disc directly following the implantation of the inventive device and the implanted disc after allowing for 30 minutes of hydration in saline. FIG. 5 depicts the angular motion in flexion and extension of human cadaveric motion segments over a constant range of bending moments. FIG. 6 represents the deviation of the motion segment flexibility in flexion-extension from the intact disc. FIG. 7 represents the angular motion in left and right lateral bending of human cadaveric motion segments over a constant range of bending moments: (a) for the intact disc, (b) the disc following nucleotomy, (c) the disc directly following implantation of the present invention, and (d) the implanted disc after allowing 30 minutes for additional hydration. The data shows the biomechanical instability introduced to the discs following the nucleotomy and demonstrates the recovery of normal range of motion following the implantation of the inventive implant device. FIG. 8 is a chart showing the deviation of the motion segment flexibility in lateral bending from the intact disc. Error bars on all figures indicated the standard deviation from the mean.

Additional embodiments of this invention may include the supplementation of the cancellous bone with synthetic material that is of similar physical dimensions as the implanted cancellous tissue forms. Such synthetics may include polymeric hydrogels, biodegradable polymers, rubbers, or other materials that are elastic in nature and capable of being packed together in a similar fashion to the cancellous tissue.

Other additional embodiments of this invention may include the addition of cells and/or biological agents to the cancellous bone either prior to implantation or post-implantation. Transplanted cells may include those derived from bone marrow, other pluripotent stem cells, chondrocytes, and nucleus pulposus cells. Bioactive molecules may include viral particles, plasmids, hormones, extracellular matrix proteins, platelet rich plasma, or growth factors such as those in the TGF-β, FGF, VEGF, IGF, and BMP families. Another embodiment of the invention may include the addition of a radiopaque marker to the cancellous tissue in order to make the implant visible during surgery. The radiopaque marker may be derived from beryllium copper, brass, bronze, carbon steel, clad metals, copper, kovar, molybdenum, nickel, niobium, stainless steel, tantalum, titanium, zirconium, or other radiopaque material. Other suitable materials may include barium, platinum, platinum iridium, gold and iodine-containing compounds.

This invention also utilizes a method of treating a degenerative spinal disc by replacing or augmenting the disc nucleus with allograft tissue through a minimally invasive approach. In a preferred embodiment, the allograft tissue form comprises small uniformly shaped fully demineralized, non-osteoinductive cancellous bone units. The target disc will be accessed and nuclear material will be removed via microdiscectomy or minimally invasive nucleotomy. Following this step, the resulting nuclear cavity is sized and an expandable, porous pouch is inserted into the disc nucleus via an existing annular tear or a small annulotomy. The pouches are initially empty and in a collapsed state such that it can be passed through a small diameter portal in the disc annulus (~3 mm-4 mm). This mesh bag may be made from synthetic materials such as polyester or biological material such as allograft bone, dermis, or fascia, hyaluronic acid, collagen, or other structural protein. In a preferred embodiment, a woven fabric mesh is utilized as the implantable pouch, with a pore size that is sufficiently small such that allograft material units do not extrude through the mesh openings. This containment device may also be sewn such that it expands into a disc nucleus-like shape upon addition of implant material and may have a radiographic marker in order to track its location following implantation. The porous nature of the pouch may allow the transfer of fluid from the surrounding disc tissue to the implant material and vice-versa. The porosity and mesh size of the pouch may also be critical for obtaining an appropriate biological response to the allograft material contained within it. By allowing cellular infiltration and fluid exchange, it may be possible for tissue remodeling or fibrous tissue formation to occur inside the implanted mesh pouch within the disc.

After the porous pouch has been inserted and positioned inside the disc, a plurality of small, demineralized non-osteoinductive cancellous bone units are passed into the bag through a hollow rod until the bag is appropriately filled. In a preferred embodiment, the hollow rod has an internal diameter between 3 mm to 4 mm, and is utilized in combination with cancellous units that are cube shaped with 2 mm to 3 mm sides or disc-shaped with a diameter of 2 mm to 3 mm and a height of 2 mm to 3 mm or spherical with a diameter of 2 mm to 3 mm. The cancellous tissue forms may have a defined shape that may be spherical, discoid, or cuboidal in nature and may be loaded into filler tubes prior to implantation. The cancellous tissue forms may also have a single dimension of no more than 5 mm and no less than 1.0 mm and will be designed to pack tightly under pressure. It is recognized the size of the individual units will be considerably smaller than the diameter of the filler bag once it has been expanded.

In operation, a small nucleotomy is created in the disc annulus by first making an incision in the disc and then expanding the same using dilators of increasing size. The nucleus is then mechanically removed while avoiding damage to the inner annulus or the cartilaginous end plates. Following the nucleotomy, an inflatable balloon is inserted in the disc nucleus and the nucleus is filled with radio contrast fluid to a specific pressure between 30 and 60 psi such that the nuclear cavity is visible under fluoroscopy. This step allows visualization of the cavity created by the nucleotomy and also provides a measurement of the cavity volume, which will be used to select the mesh pouch size and determine the amount of fill material needed for the implant. After sizing, the porous mesh pouch is inserted through the portal in the disc annulus. In order to ensure that the mesh pouch is not restricted from deploying properly, an inflatable balloon is placed into the empty mesh pouch in situ and the balloon is again filled with radio contrast material. Subsequently, the balloon is removed from the mesh pouch and demineralized non-osteoinductive cancellous tissue in the form of cubes, discs or spheres is added to the mesh pouch by extruding the filler implant material that has been pre-loaded in small diameter tubes. Based on the empty cavity volume of the disc nucleus, the mesh pouch will be filled to a packing density of 0.3 to 0.9 g/cc where the weight of the tissue is based upon its dry weight. After the filling step, the mesh pouch is released from its holder tube and its opening is tied off to prevent migration of the cancellous tissue from the disc space. In another embodiment of the invention, a degenerated or diseased intervertebral disc is treated with the above noted steps wherein after the step of removing a portion of or the entire disc nucleus via mechanical disruption, at least one region of the vertebral end plates is removed or disrupted.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present inventions defined by the following claims:

What we claim is:

1. An implant for treating a degenerative intervertebral disc which includes an annulus fibrosus and a nuclear cavity whose boundary is bordered by surrounding walls of the annulus fibrosus and by superior and inferior vertebrae, said implant comprising:
    an expandable porous pouch having an exterior surface and a size and shape, when in a collapsed state, to facilitate its insertion through an opening in the annulus fibrosus of the intervertebral disc and its introduction into the nuclear cavity of the intervertebral disc; and
    a plurality of substantially demineralized bone units that are sized and shaped for insertion into said porous pouch, said porous pouch being expandable from said collapsed state to an expanded state, in which said exterior surface of said porous pouch engages a substantial portion of the boundary of the nuclear cavity of the intervertebral disc responsive to the insertion of said bone units into said porous pouch, and said bone units being non-osteoinductive as a result of having been soaked in hydrogen peroxide, whereby said bone units do not promote fusion of the superior and inferior vertebrae and do not promote bony ingrowth.

2. The implant of claim 1, wherein at least some of said bone units include cancellous bone.

3. The implant of claim 1, wherein at least some of said bone units include allograft bone.

4. The implant of claim 1, wherein each of said bone units is deformable from a uncompressed state, in which pores of said porous pouch retain each of said bone units within said porous pouch, to a compressed state, in which insertion of each of said bone units into said porous pouch is facilitated.

5. The implant of claim 4, wherein each of said bone units has shape memory such that each of said bone units assumes its said uncompressed state after insertion into said porous pouch.

6. The implant of claim 4, wherein said porous pouch contains a sufficient quantity of said bone units such that said bone units act as a single coherent mass when subjected to a mechanical load.

7. The implant of claim 4, wherein said porous pouch contains a sufficient quantity of said bone units such that said implant withstands compressive loads that are generated within a patient's spine.

8. The implant of claim 7, wherein said porous pouch contains a sufficient quantity of said bone units such that said implant facilitates the transfer of compressive loads to the annulus fibrosus of the intervertebral disc.

9. The implant of claim 1, wherein said porous pouch contains a sufficient quantity of said bone units such that said implant conforms to the boundary of the nuclear cavity of the intervertebral disc.

10. The implant of claim 1, wherein at least some of said bone units have a spherical shape.

11. The implant of claim 1, wherein at least some of said bone units have a cuboidal shape.

12. The implant of claim 1, wherein at least some of said bone units have a disc shape.

13. The implant of claim 1, wherein at least some of said bone units include a radiopaque marker.

14. The implant of claim 13, wherein said radiopaque marker is selected from a group consisting of barium, beryllium copper, brass, bronze, carbon steel, clad metals, copper, gold, kovar, molybdenum, nickel, niobium, platinum iridium, stainless steel, tantalum, titanium and zirconium.

15. The implant of claim 1, wherein said porous pouch includes a radiographic marker.

16. The implant of claim 1, wherein said bone units have a pH in a range of from about 6.6 to about 7.4.

17. The implant of claim 1, wherein each of said bone units has a dimension of 5 mm or less.

18. The implant of claim 17, wherein each of said bone units has a dimension within a range of from about 1 mm to about 4 mm.

19. The implant of claim 18, wherein each of said bone units has a dimension within a range of from about 2 mm to about 3 mm.

20. The implant of claim 1, wherein each of said bone units has a calcium content of less than 0.1% wt/wt.

21. The implant of claim 1, wherein said bone units are sealed within said pouch.

22. The implant of claim 1, wherein at least one of said bone units includes at least one bioactive agent.

23. The implant of claim 22, wherein said at least one bioactive agent includes one or more substances taken from a group consisting of growth factors, hormones, viral particles, platelet rich plasma, plasmids, and extracellular matrix proteins.

24. The implant of claim 23, wherein said growth factors include those in the TGF-β, FGF, VEGF, IGF and BMP families.

25. The implant of claim 1, wherein at least one of said bone units include cells.

26. The implant of claim 25, wherein said cells include nucleus pulposus cells.

27. The implant of claim 25, wherein said cells include cells that have been derived from bone marrow.

28. The implant of claim 25, wherein said cells include pluripotent stem cells.

29. The implant of claim 25, wherein said cells include chondrocytes.

30. The implant of claim 1, wherein said porous pouch is a mesh bag.

31. The implant of claim 1, wherein said porous pouch is formed from a woven synthetic material.

32. The implant of claim 1, wherein said porous pouch is formed from allograft bone.

33. The implant of claim 1, wherein said porous pouch is formed from dermis.

34. The implant of claim 1, wherein said porous pouch is formed from fascia.

35. The implant of claim 1, wherein said porous pouch is formed from hyaluronic acid.

36. The implant of claim 1, wherein said porous pouch is formed from collagen.

37. The implant of claim 1, wherein said porous pouch is formed from a structural protein.

38. The implant of claim 1, wherein said porous pouch includes pores having a size selected so as to inhibit said bone units from passing through said pores.

39. The implant of claim 1, wherein said porous pouch has a porosity and pore size selected so as to facilitate cellular infiltration and fluid exchange, thereby promoting tissue remodelling within said porous pouch in the nuclear cavity of the intervertebral disc.

40. The implant of claim 1, wherein said porous pouch has a porosity and pore size selected so as to facilitate cellular infiltration and fluid exchange, thereby promoting fibrous tissue formation within said porous pouch in the nuclear cavity of the intervertebral disc.

41. A method of treating a degenerative intervertebral disc which includes an annulus fibrosus and a nuclear cavity whose boundary is bordered by surrounding walls of the annulus fibrosus and by superior and inferior vertebrae, the method comprising the steps of:
   visualizing the nuclear cavity, wherein said visualizing step includes inserting a balloon into the nuclear cavity, filling the balloon with radio contrast fluid to a specified pressure such that the nuclear cavity is visible under fluoroscopy, and removing the balloon from the nuclear cavity;
   inserting an expandable porous pouch through the annulus fibrosus and into the nuclear cavity; and
   expanding the porous pouch by filling it with a plurality of substantially demineralized bone units until an exterior surface of the porous pouch engages a substantial portion of the boundary of the nuclear cavity of the intervertebral disc, the bone units being non-osteoinductive, whereby the bone units do not promote fusion of the superior and inferior vertebrae and do not promote bony ingrowth.

42. The method of claim 41, wherein said visualizing step is performed prior to said inserting step.

43. The method of claim 41, wherein said visualizing step includes measuring the volume of the nuclear cavity.

44. A method of treating a degenerative intervertebral disc which includes an annulus fibrosus and a nuclear cavity whose boundary is bordered by surrounding walls of the annulus fibrosus and by superior and inferior vertebrae, the method comprising the steps of:
   inserting an expandable porous pouch through the annulus fibrosus and into the nuclear cavity;
   deploying the porous pouch, wherein said deploying step includes placing a balloon into the inserted porous pouch, filling the balloon, and removing the balloon from the porous pouch; and expanding the porous pouch by filling it with a plurality of substantially demineralized bone units until an exterior surface of the porous pouch engages a substantial portion of the boundary of the nuclear cavity of the intervertebral disc, the bone units being non-osteoinductive, whereby the bone units do not promote fusion of the superior and inferior vertebrae and do not promote bony ingrowth;

said deploying step being performed after said inserting step and before said expanding step.

45. The method of claim 44, further comprising a step of removing at least a portion of a nucleus pulposus from the nuclear cavity.

46. The method of claim 45, wherein said removing step is performed prior to said inserting step.

47. The method of claim 45, wherein said removing step includes removing at least one region of vertebral end plates.

48. The method of claim 44, further comprising a step of sealing the bone units in the filled porous pouch to inhibit migration of the bone units from the nuclear cavity, said sealing step being performed after said expanding step.

49. The method of claim 44, wherein said expanding step includes filling the porous pouch with a sufficient quantity of the bone units until an exterior surface of the porous pouch conforms to the boundary of the nuclear cavity of the intervertebral disc.

50. The method of claim 44, wherein said expanding step includes compressing the bone units from an uncompressed state, in which pores of the porous pouch retain each of the bone units within the porous pouch, to a compressed state, in which insertion of each of the bone units into the porous pouch is facilitated.

51. The method of claim 50, wherein each of the bone units has shape memory such that each of the bone units assumes its uncompressed state after insertion into the porous pouch.

52. The method of claim 44, wherein said inserting step is performed by inserting the porous pouch through an existing tear in the annulus fibrosus of the intervertebral disc.

53. The method of claim 44, further comprising the step of making a small portal in the annulus fibrosus of the intervertebral disc, wherein said inserting step is performed by inserting the porous pouch through the portal.

54. A method of treating a degenerative intervertebral disc which includes an annulus fibrosus and a nuclear cavity whose boundary is bordered by surrounding walls of the annulus fibrosus and by superior and inferior vertebrae, the method comprising the steps of:
inserting an expandable porous pouch through the annulus fibrosus and into the nuclear cavity;
loading at least some of a plurality of substantially demineralized bone units into a plurality of tubes; and
expanding the porous pouch by delivering the bone units from the plurality of tubes into the porous pouch and filling the porous pouch with the bone units from the plurality of tubes until an exterior surface of the porous pouch engages a substantial portion of the boundary of the nuclear cavity of the intervertebral disc, the bone units being non-osteoinductive, whereby the bone units do not promote fusion of the superior and inferior vertebrae and do not promote bony ingrowth.

55. The method of claim 54, wherein said loading step is performed prior to said expanding step.

56. A method of treating a degenerative intervertebral disc which includes an annulus fibrosus and a nuclear cavity whose boundary is bordered by surrounding walls of the annulus fibrosus and by superior and inferior vertebrae, the method comprising the steps of:
inserting an expandable porous pouch through the annulus fibrosus and into the nuclear cavity;
lyophilizing a plurality of substantially demineralized bone units;
weighing a quantity of the lyophilized bone units;
hydrating the quantity of lyophilized bone units in fluid;
loading at least some of the quantity of lyophilized bone units into at least one tube; and
expanding the porous pouch by delivering the bone units from the at least one tube into the porous pouch and filling the porous pouch with the bone units from the at least one tube until an exterior surface of the porous pouch engages a substantial portion of the boundary of the nuclear cavity of the intervertebral disc, the bone units being non-osteoinductive, whereby the bone units do not promote fusion of the superior and inferior vertebrae and do not promote bony ingrowth,
said lyophilizing, weighing and hydrating steps being performed before said loading step.

57. An implant for repair of a degenerative intervertebral disc which is bordered by a patient's superior and inferior vertebrae, said implant comprising a porous pouch and a plurality of bone units that are sized and shaped for insertion into said porous pouch, said bone units being formed by a method including the steps of:
(a) demineralizing a sheet of bone;
(b) treating the demineralized bone sheet to render it non-osteoinductive; and
(c) cutting the demineralized, non-osteoinductive bone sheet into said bone units,
whereby said bone units do not promote fusion of the superior and inferior vertebrae and do not promote bony ingrowth.

58. The implant of claim 57, wherein step (b) includes performing a chemical treatment on the bone units to render at least some of them non-osteoinductive.

59. The implant of claim 57, wherein step (b) includes performing a thermal treatment on the bone units to render at least some of them non-osteoinductive.

60. The implant of claim 57, wherein step (b) includes treating the bone units with high energy irradiation to render at least some of them non-osteoinductive.

61. The implant of claim 57, wherein step (b) includes soaking the bone units in hydrogen peroxide to render at least some of them non-osteoinductive.

62. The implant of claim 61, wherein said soaking step is performed for at least an hour.

\* \* \* \* \*